United States Patent [19]

Funk et al.

[11] 4,121,151
[45] Oct. 17, 1978

[54] ANALYSIS INSTRUMENT

[75] Inventors: David B. Funk, Virden; William E. Midden, Springfield, both of Ill.

[73] Assignee: Dickey-john Corporation, Auburn, Ill.

[21] Appl. No.: 791,651

[22] Filed: Apr. 27, 1977

[51] Int. Cl.² .................................. G01R 27/26
[52] U.S. Cl. ................................. 324/61 R
[58] Field of Search ............ 324/61 R, 61 QS, 61 QL

[56] References Cited

U.S. PATENT DOCUMENTS

| | | | |
|---|---|---|---|
| 2,693,575 | 11/1954 | Greenwood et al. | 324/61 R |
| 2,759,147 | 8/1956 | Stein | 324/61 R |
| 2,825,870 | 3/1958 | Hart | 324/61 R X |
| 2,947,940 | 8/1960 | Stein | 324/61 R X |
| 3,028,549 | 4/1962 | Stein | 324/61 R |
| 3,051,894 | 8/1962 | Fathauer | 324/61 R |
| 3,566,260 | 2/1971 | Johnston | 324/61 R |
| 3,681,685 | 8/1972 | Tarry et al. | 324/61 QS |
| 3,739,264 | 6/1973 | Resh | 324/61 R |
| 3,781,673 | 12/1973 | Resh | 324/61 R |
| 3,794,911 | 2/1974 | Fathauer | 324/61 QS |

Primary Examiner—Stanley T. Krawczewicz
Attorney, Agent, or Firm—Olson, Trexler, Wolters, Bushnell & Fosse, Ltd.

[57] ABSTRACT

An analysis instrument for measuring selected constituents present in a sample of a material such as a bulk commodity includes a test cell to receive the sample. The test cell comprises a capacitor whose electrical properties are modified in accordance with the dielectric constant of the sample, which dielectric constant is a function of the contents of the sample. A hopper is mounted above the test cell for holding a quantity of the commodity to be tested and doors forming a bottom of the hopper are selectively openable to introduce the material from the hopper into the test cell. A strike off mechanism is provided for striking off the sample level with the top of the test cell to assure a constant volume of sample material therein. Weight and temperature sensors are provided for measuring the weight and temperature of the sample. An unloading mechanism is provided for rotating the test cell to remove the sample therefrom upon completion of the measurements.

20 Claims, 6 Drawing Figures

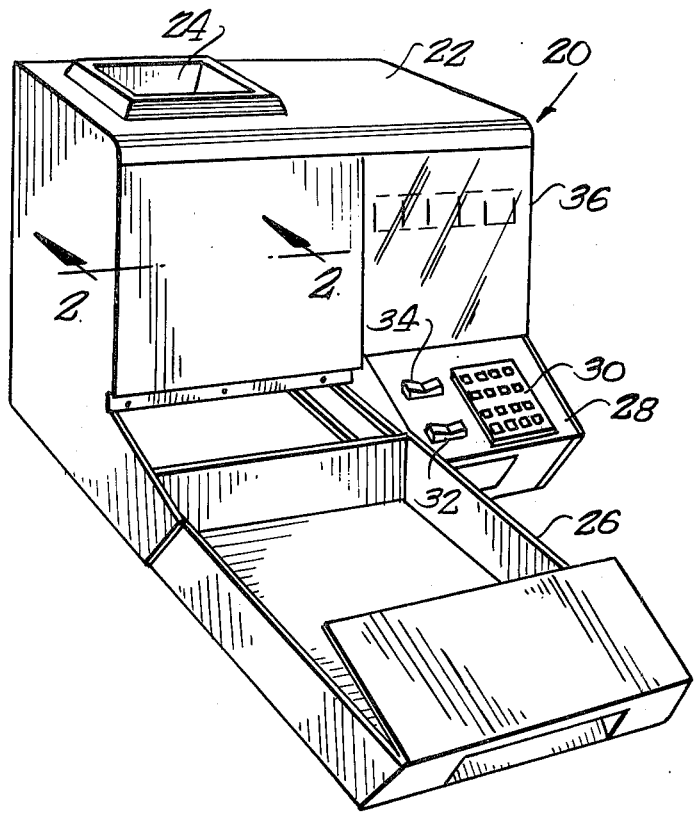
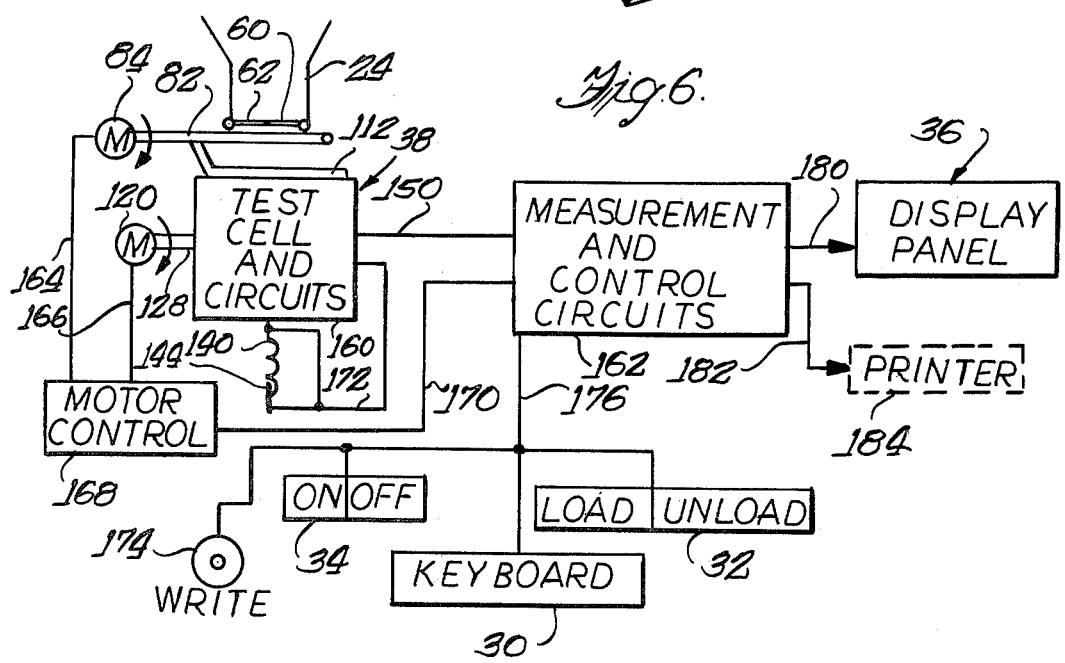

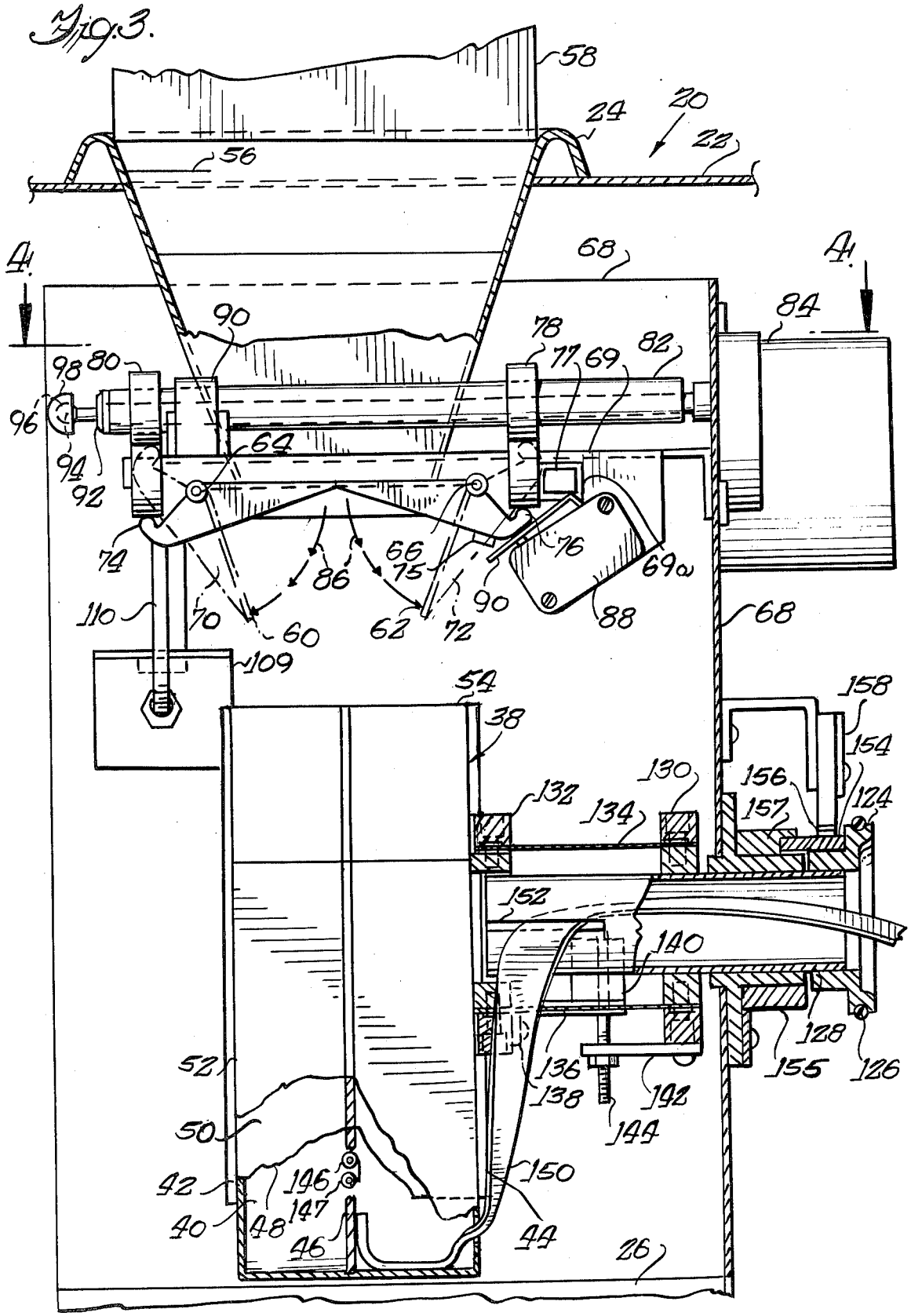

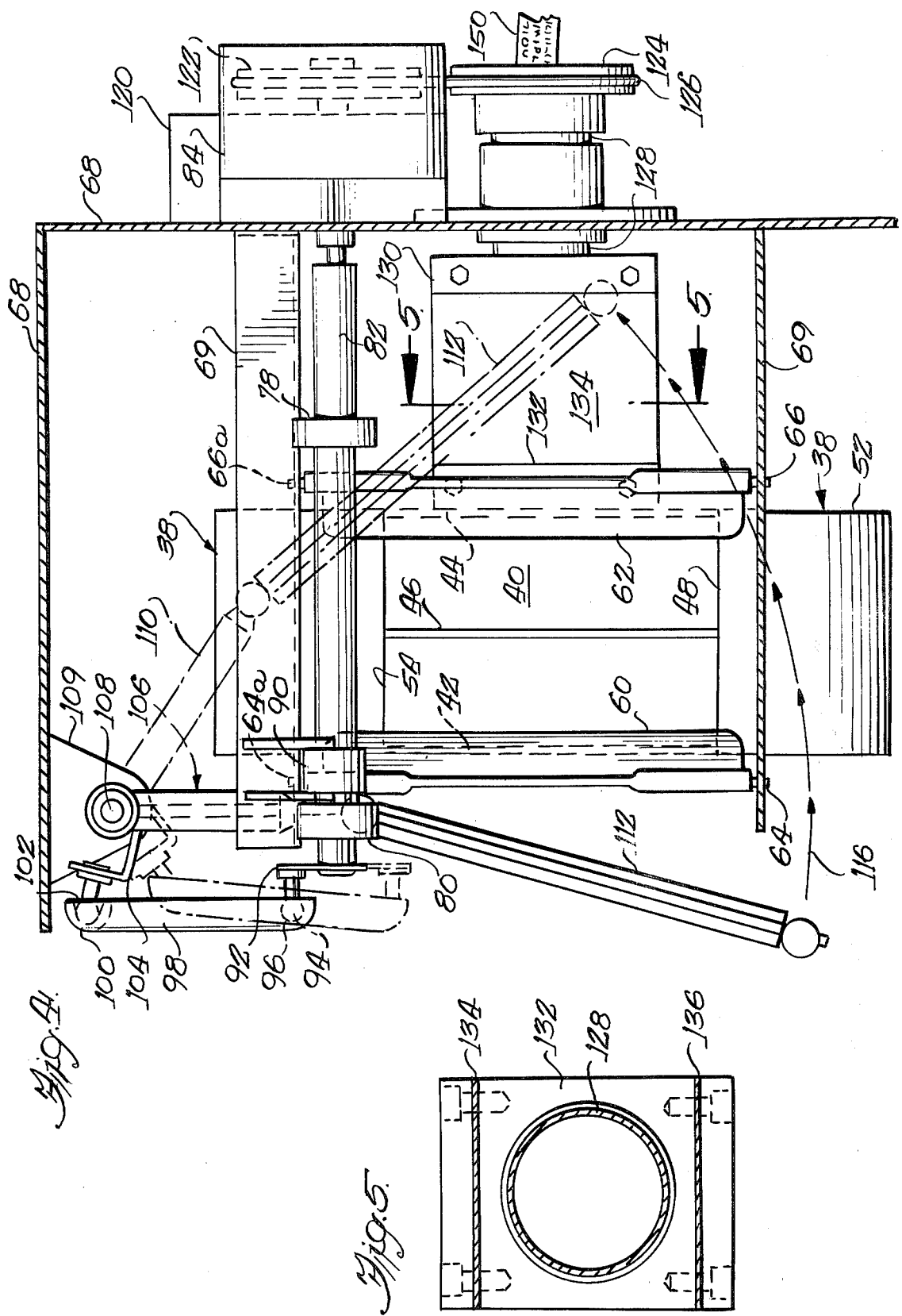

ANALYSIS INSTRUMENT

BACKGROUND OF THE INVENTION

This invention relates to material analysis apparatus, and more particularly to apparatus for measuring the contents of a bulk commodity, such as a grain. The description will be facilitated by addressing the specific problem of measuring the moisture content of a farm grain, such as corn, soybeans or the like.

In measuring the moisture content of a grain, it is known to use a test cell that comprises a capacitor in which the grain sample is introduced and to obtain a reading representative of a moisture content based upon an electrical measurement of the grain filled capacitor. In the past, such measurements have been made by connecting the test cell as a capacitor in the tank circuit of an oscillator and inferring the capacitance of the test cell from a measurement of the frequency of the oscillator. This approach is limited by the assumption that the test cell represents an ideal or pure capacitance, failing to take into account the conductance of a real capacitor, also present in the test cell. Thus, some degree of error is inherent in this method of measurement. Also, the real capacitor of the test cell has a complex admittance comprising a capacitive component and a frequency dependent resistive component often called the loss factor. Thus, the above measurement also fails to take into account the frequency dependent resistive component.

The dielectric constant of a material causes a change in the electrical properties of a capacitor when the material is introduced in its field region, compared to the properties of the same capacitor when its field region is devoid of material. In general, the dielectric constant of a material is a function of the physical properties or constituents of the material as, for example, the moisture content of a grain sample. Thus, the dielectric constant and, therefore, the properties or constituents of a material may be derived by introducing the material into a test cell constructed as a capacitor and measuring the change in voltage across the test cell, as compared to the voltage across the empty test cell with the same signal applied thereto. If the test cell is included in an electrical network in which other components are of known fixed values and a known signal is applied to the network, voltage or gain measurements taken across the test cell filled with the sample material can be used to calculate the dielectric constant of the material. It can be shown that the conductance of the test cell capacitor with a material of known bulk conductivity therein is proportional to the capacitance of the evacuated capacitor. Thus, it is possible to eliminate the effects of the conductance and allow for the effects of both the capacitive and the frequency dependent resistive components of the real capacitor comprising the test cell by correlating separate voltage measurements taken across the test cell when empty and when filled with the sample, and with signals of at least two different frequencies applied to the test cell.

Since grain moisture is defined as a percentage by weight of moisture, it has been necessary in previous moisture testing apparatus to first weigh a sample and then introduce the sample into the test cell. A preliminary moisture reading may then be obtained on the instrument either by use of a properly calibrated meter or calculating moisture from a readout on the instrument in conjunction with a chart. After this preliminary moisture calculation has been obtained, however, it is necessary to apply a correction factor for the temperature of the sample. Thus, it is necessary to measure the temperature of the sample and by reference to a suitable table or chart obtain a temperature corrected moisture reading. Also, in the case of farm grains, the moisture reading must be corrected in accordance with the variance of the bulk density of the sample from a standard bulk density. Thus, it is necessary to determine the volume of the sample being tested, in addition to its weight, to determine the density thereof. Then, an additional calculation must be made, or chart referred to, to obtain a moisture content reading corrected for bulk density.

It can be seen that the foregoing procedures are relatively cumbersome when carried out with prior art apparatus due to the inconvenience of performing multiple separate measuring steps, in order to obtain a value of moisture content as corrected for bulk density and temperature. Also, it is inconvenient to perform several calculations and/or to refer to charts or tables to derive this final corrected value of moisture content.

OBJECTS AND SUMMARY OF THE INVENTION

Accordingly, it is a general object of this invention to provide an analysis instrument which is convenient to use, and automatically performs all measurements necessary to obtain the contents of a sample.

A more specific object of this invention is to provide an analysis instrument, in accordance with the foregoing object, for measuring the moisture content of a sample in accordance with the dielectric constant of the sample.

Another object of the present invention is to provide an analysis instrument, in accordance with the foregoing objects, adapted to adjust the sample to a predetermined constant volume.

Still another object of this invention is to provide an analysis instrument in accordance with the foregoing objects adapted to automatically measure the bulk density of the sample.

Yet another object of this invention is to provide an analysis instrument, in accordance with the foregoing objects, further adapted to automatically measure the temperature of the sample.

Briefly, and in accordance with the foregoing objects, an analysis instrument according to the present invention comprises a test cell for receiving a sample of a material whose contents are to be measured. The test cell comprises a capacitor whose electrical properties are modified in accordance with the dielectric constant of the sample, which dielectric constant is a function of the contents thereof. The analysis instrument includes means for measuring the bulk density of a sample including means for adjusting the volume of the sample in the test cell to a predetermined constant volume and means for weighing the sample in the test cell. The analysis instrument further includes means including the test cell capacitor and coupled with the bulk density measuring means for measuring the dielectric constant of the sample in the test cell.

In a preferred embodiment, the analysis instrument also includes temperature sensing means for measuring the temperature of the sample in the test cell, means for introducing a sample of a material to be tested into the test cell, and removal means for selectively removing the sample from the test cell.

The foregoing, as well as other objects, features and advantages of the present invention will be appreciated from a consideration of the following detailed description together with the accompanying drawings in which like reference numerals are used throughout to designate like elements and components.

BRIEF DESCRIPTION OF THE DRAWINGS

FIG. 1 is a perspective view of an analysis instrument incorporating features of the present invention;

FIG. 3 is a view of the instrument of FIGS. 1 and 2, taken generally along the line 3—3 of FIG. 2;

FIG. 4 is a view of the instrument of FIGS. 1, 2 and 3, taken generally along the line 4—4 of FIG. 3;

FIG. 5 is a view of a portion of FIG. 4 taken generally along the line 5—5 of FIG. 4; and FIG. 6 is a simplified block diagram showing the overall arrangement of the instrument of FIGS. 1 through 5.

DETAILED DESCRIPTION

Figure 2:
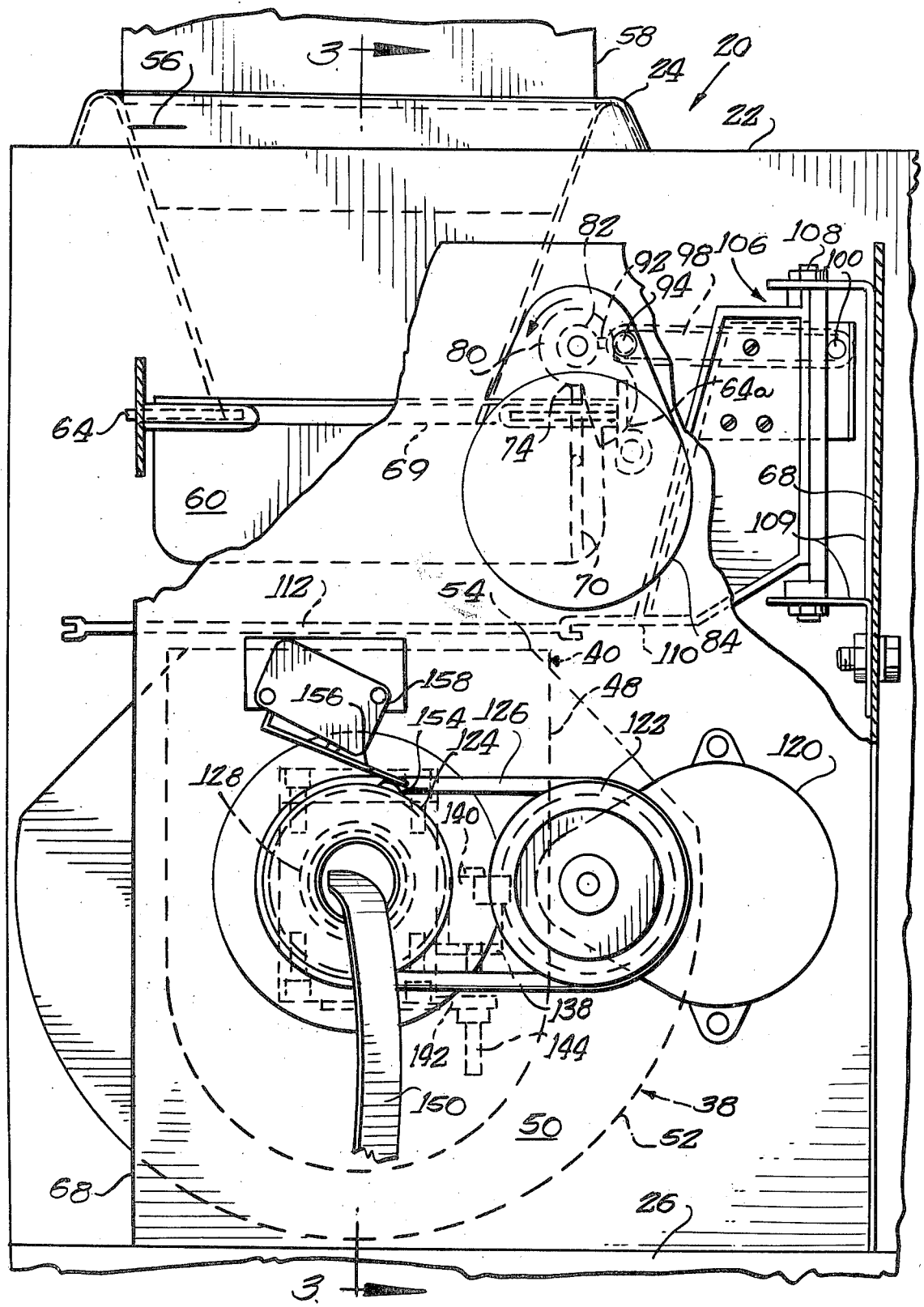
FIG. 2 is an enlarged view, partially cut away, of a portion of the instrument of FIG. 1, taken generally along the line 2—2 of FIG. 1.

The following detailed description is facilitated by addressing the problem of measuring the moisture of a sample of a farm grain. Thus, the analysis instrument of the present invention will be referred to hereafter as a moisture tester. Referring now to FIG. 1 a moisture tester 20 comprises a housing 22, having a hopper 24 mounted at the top thereof for receiving a quantity of material whose moisture content is to be measured. The moisture tester 20 also includes a drawer 26 slidably mounted in the bottom portion thereof to receive the sample material subsequent to testing and to effect the removal thereof from the tester. The sample drawer 26 is also removable from the moisture tester 20 to provide for the use of other suitable means in its place to effect removal of sample material after testing thereof. The moisture tester 20 also includes a control panel 28 including a keyboard comprising a four-by-four array of control switches which may comprise pushbutton type switches 30, a load-unload switch 32 and an on/off switch 34. The operation of these controls is further explained herein below. The moisture tester 20 also includes a display panel 36, the structure and operation of which are explained hereinbelow.

Referring now to FIGS. 2, 3 and 4, the sample handling portion of the moisture tester 20 is illustrated in greater detail. A test cell assembly 38 includes a test cell 40 to receive a sample of the material to be tested, which comprises a capacitor made up of generally flat, U-shaped end plates or electrodes 42 and 44 constructed of suitable conductor material, and a somewhat larger flat center plate 46 which comprises printed circuit board material having both sides thereof copper plated to define a center electrode of generally the same dimensions as the electrodes 42 and 44 and to define suitable interconnecting wiring patterns generally outside of the electrode surfaces for circuit elements to be mounted on the plate 46 described hereinbelow. An enclosure or wall member 48 comprises two pieces of suitable insulating material shaped to define enclosures between the respective end electrodes 42, 44 and the center plate 46. An outer enclosure member 52 of the test cell assembly 38 is constructed of a suitable insulating material, the electrodes 42 and 44 preferably being mounted on the outside of the enclosure member 52 and the center plate 46 being generally co-planar with a cross section of the enclosure 52 and mounted substantially centrally therein. The wall member 48 and enclosure 52 define between them a chamber 50, which provides a suitable enclosed space for containing the aforementioned wiring patterns formed on the center plate 46 and the circuit elements mounted thereon. It will be noted that the test cell 40 is provided with a substantially rectangular opening 54, defined by the end electrodes 42, 44 and the side portions of wall member 48, and substantially level with the top of the test cell 40, through which a sample of material tested is introduced, as described below.

A hopper 24 is mounted directly above the test cell assembly 38 to receive a quantity of grain to be tested, and is provided with a fill line or indicator mark 56 to show the minimum amount of material necessary to assure proper filling of the test cell 40. A hopper extension member 58 may be removably mounted over the hopper 24 to assure filling thereof with material well over the minimum filling mark 56. A pair of doors 60 and 62 are mounted below the hopper 24 to define a bottom thereof. The doors 60 and 62 are mounted upon hinge pins 64 and 64a, and 66 and 66a so as to be selectively rotatable about the hinge pins 64 and 64a and 66 and 66a, the ends of which are in turn respectively affixed in a substantially horizontal alignment to opposite ends of a mounting plate 69 affixed to an inner housing 68 suitably positioned within the housing 22. The doors 60 and 62 are provided with support members 70 and 72 each including an ear or actuator member 74 and 76 at an end thereof radially outward from the respective hinge pins 64 and 66. A pair of cams 78 and 80 are mounted for rotation upon a horizontally extending shaft 82 which is driven by a motor 84 attached to the inner housing 68, the cams 78 and 80 being in engagement with the ears or actuator members 74 and 76 of the door support members 70 and 72, respectively. Thus, the doors 60 and 62 are selectively openable in the direction indicated by the arrows 86 via the action of cams 78 and 80, whose rotation by shaft 82 via the motor 84 allows doors 60 and 62 to rotate about hinge pins 64 and 66, respectively. A magnetically actuatable reed-type switch 77 is mounted on non-magnetizable plate 69 affixed to plate 69 and a magnet 75 is mounted on the support member 72 of the door 62 for acutating the switch 77 to provide an indication to electronic control circuitry to be described later herein, when the doors 60 and 62 are fully opened. A switch 88 is mounted on the plate 69 and includes an actuator 90, to be actuated by the support member 72 when the doors 60, 62 are fully closed to provide a similar indication. The shaft 82 is also mounted by suitable bearing means 90 upon the plate 69 at a portion thereof remote from the motor 84 to insure smooth and even rotation of the shaft 82. The shaft 82 is also provided with a radially extending arm or member 92 fixed to its end opposite the motor 84 which includes a first ball member 94 attached to the radially outward end thereof to rotate at a fixed radius about the center of the shaft 82. The ball member 94 is fixed in a socket 96 which forms a first end of a linkage member 98, the opposite end thereof defining a second socket 100 in which is fixed a second ball member 102. The second ball member 102 includes a linkage 104 formed at its end opposite the socket 100 and attached by suitable means to a strike off assembly 106. Strike off assembly 106 includes a shaft 108 rotatably mounted on mounting means 109 attached to housing 68, and a linkage 110 affixed to rotate together with the shaft 108 and including an elongate, strike off arm 112 positioned parallel to and just above the level open top portion 54 of the test cell 40. It will be appreciated from the foregoing that as the shaft 82 rotates, the member 92 and ball 94 affixed thereto rotate about the shaft 82, thereby actuating the linkage member 98 to pull the ball member 102 and attached linkage 104 in such a manner as to actuate the strike off assembly 106 to move or rotate the linkage 110 thereof and its elongate strike off arm 112 about the shaft 108 substantially as indicated by the arrow 116 so that the elongate strike off arm 112 passes over the open top 54 of the test cell 40, moving completely from one end to the other thereof to the position indicated in FIG. 4 by the dotted lines. Similarly, continued rotation of the shaft 82 by the motor 84 returns the wiper arm assembly 106 to its original position and, via the cams 78 and 80, again closes the doors 60 and 62. The strike off arm 112 preferably comprises a semi-rigid elongate member and an extension spring generally coextensive with and attached to the elongate member to compensate for irregularly shaped sample material as it strikes off the excess while moving across the top of the test cell 40.

It will be noted that the relative positioning of the cams 78 and 80 and member 92 upon the shaft 82 are such that the movement of the strike off assembly 106 and the strike off arm 112 thereof are synchronized with the opening of the doors 60 and 62, so that the strike off arm moves across the open top 54 of the test cell 40 shortly after the opening and closing of the doors 60 and 62. Thus, it will become apparent that the motor 84 via the shaft 82 controls a sequence of operation wherein sample material is first released via the doors 60 and 62 from the hopper 24 into the test cell 40, over-filling the test cell 40 and subsequently, the strike off arm 112 is moved across and level with the open top 54 of the test cell 40 as described and strikes off and carries away excess sample material from the top 54 thereof the doors 60, 62 being simultaneously closed, resulting in the test cell 40 being filled with sample material of a constant predetermined volume as set by the leveling action of the strike off arm 112. Thus, the described indication given by the switch 88 also corresponds to the strike off operation being completed.

Referring now again to the test cell assembly 38, it will be seen that a motor 120 is provided along with a pair of pulleys 122, 124 and a drive belt 126 therebetween to drive a shaft 128 which is connected to rotate the test cell assembly 38 as follow. A first collar 130 is attached to the shaft 128 for rotation therewith. A second collar 132 is attached to the test cell assembly 38 to rotate in unison therewith, the interior opening of the collar 132 being clear of the shaft 128. The amount of clearance provided for the shaft 128 by the interior opening of the collar 132 effectively defines limits of movement of the test cell assembly 38 with respect to the motor 120 and shaft 128. A pair of flexure plates 134 and 136 are attached between the respective collars 130 and 132 so that the test cell assembly 38 may be rotated through 180° by the motor 120 via the shaft 128 and via the collars 130 and 132 and connecting flexure plates 134 and 136 in order to unload or remove the sample material from the test cell 40, when testing is completed. FIG. 5 illustrates a view of the collar 132 and flexure plates 134 and 136 taken generally along the line 5—5 of FIG. 4.

The collars 130 and 132 and flexure plates 134 and 136 also form a portion of weighing means for measuring the weight of the sample contained in the test cell 40. A suitable mounting means 138 is attached to the collar 132 for holding a coil 140. Similarly, a mounting member 142 is attached to the collar 130 and holds a shaft or core member 144. The opposite end of shaft or core member 144 extends through the center of the coil 140. Thus, the coil 140 and shaft 144 comprise a variable inductor. The flexure plates 134 and 136 are adapted to flex or give somewhat in response to the weight of sample material introduced into the test cell 40 so as to provide some relative movement between the collar 130 attached to the shaft 128 and the collar 132 attached to the test cell assembly 38. Thus, it will be appreciated that the coil 140 attached to the collar 132 and the core member 144 attached to the collar 130 will experience a relative change in their positions due to the flexing of flexure plates 134 and 136, said movement being in proportion to the weight of the sample material introduced into the test cell 40. The change in inductance provided by the relative movement between the coil 140 and core member 144 will correspond to the relative movement therebetween, and therefore to the weight of the sample material in the test cell 40. Suitable wires or leads are provided (not shown) to energize the coil 40 to produce a weight signal thereacross proportional to the inductance thereof and to connect the coil to a suitable weighing circuit in the chamber 50 to be described hereinbelow. It will be appreciated that the aforementioned limits of movement defined by the clearance of the collar 132 about the shaft 128 serves to protect the coil 140 and core member 144 from possible damage due to large deflections of the plates 134, 136 which might otherwise occur during loading of a sample into the test cell, or when the moisture tester is being transported.

The test cell 40 also includes, mounted in the middle plate 46 thereof, a pair of temperature sensors 146, 147 to provide a signal corresponding to the temperature of the sample to be contained therein. It will be appreciated that the positioning of the temperature sensors 146, 147 substantially in the central, interior portion of the test cell 40, provides an optimum temperature reading, as the sample material, once introduced into the test cell 40, will substantially surround the sensors 146, 147. Suitable printed circuit conductors are provided on the plate 46 from the temperature sensors 146, 147 to the chamber 50 containing the test cell circuits. A suitable electrical cable 150, in the form of a flat ribbon-type cable as provided to connect the circuit components in the chamber 50 of the test cell assembly 38 with the other measurement and control circuits of the moisture tester. The flat cable 150 is directed through a suitable slot 152 provided therefore in the shaft 128, the shaft 128 being hollow to allow the passage of cable 150 therethrough to exit at the end thereof through a suitable opening provided therefore in the pulley 124. The cable 150 includes a plurality of leads or wires adapted to make appropriate connections between the circuits of the test cell 40 and measurement and control circuits of the moisture tester to be described in detail hereinbelow.

The pulley 124 is further provided with a raised stop member 154 which is adapted to engage second and third stop members 155 and 157 mounted 180° apart upon the housing 68 adjacent the pulley 124, when the pulley 124, shaft 128 and test cell assembly 138 are rotated through approximately 180° to unload or empty the sample material from the test cell 40 and again right the test cell upon completion of testing. The raised stop member 154 also engages an acutator 156 of a switch 158 when the test cell assembly is in its upright position to provide a signal for control circuits of the moisture tester, to be described below, corresponding to the location of the test cell 40 in either the upright (switch closed) or in the sample removal (switch open) position. It will be noted that the motor 120 preferably comprises an induction-type permanent magnet synchronous motor which is adapted, in conjunction with a motor control circuit described below, to automatically reverse its direction of rotation when the stop member 154 engages the complimentary stop members 155 and 157 so as to automatically right the test cell assembly 38 following the unloading of the sample material therefrom, and vice versa.

Turning now to FIG. 6, a block diagram illustrates the overall arrangement of the moisture tester of FIGS. 1 through 5, including the test sample portion hereinabove described as well as additional measurement and control circuitry to be described in further detail hereinbelow. The portions of the apparatus described hereinabove are indicated by the same numbers in FIG. 6. Test cell circuits 160 including a weighing circuit are mounted, as described above, on the printed circuit portion of the plate 46 in the chamber 50 provided therefore in the test cell assembly 38, and connected to the other circuits of the moisture tester via the cable 150 described above. The test cell circuits 160 include a suitable peak detector circuit to be described below, to receive the signals developed across the test cell 40 and provide suitable peak portons thereof. It will be appreciated that the mounting of these circuit components on the plate 46 in the chamber 50, adjacent the test cell 40 substantially eliminates "cable effects" such as noise, cable capacitance, static or the like which might otherwise effect the relatively low-level test cell signals if transmitted, unmodified, over the cable 150.

Cable 150 connects test cell circuits 160 with measurement and control circuits 162. Lines 164 and 166 connect the motors 84 and 122, respectively, with a motor control circuit 168 which is in turn connected to the measurement and control circuit 162 via line 170. The weight sensor comprising coil 140 and core member 142 is connected to the weighing circuit portion of the test cell circuits 160 by line 172. The keyboard 30, load/unload switch 32 and on/off switch 134, together with a write switch 174, are connected via line 176 to the measurement and control circuits 162. Display circuits 178 associated with the display panel 36 are connected via a line 182 to the measurement and control circuits 162. A line 182 connects the measurement and control circuits 162 to a printer 184 which may optionally be provided separate from the moisture tester to provide a written record of the measurements taken thereby.

Briefly, the operation of the moisture tester is as follows. Instructions from the control panel 28 and specifically from the actuation of the load-unload switch 32 to the load position provide instructions to the control circuit portion of the measurement and control circuits 162 via line 176 causing the control circuit to activate the motor control 168 via the line 170 to rotate the motor 84 via line 84 for rotating the shaft 82 to actuate the doors 60 and 62 and the strike off assembly 106 as described above. A quantity of the sample material is thus released from the hopper 24 into the test cell 40 and adjusted to a predetermined constant volume by the strike off arm 112, as described above. The measurement and control circuits 162 initiate measurements of temperature, weight and moisture content of the sample in the test cell and provide for correlation and display of the measurements via the line 180 and the display circuits 178 or for printing of the measurements via the line 182 and printer 184 in accordance with operator instructions via the keyboard 30. When the measurements have been completed, the operator may actuate the load-unload switch 32 to the unload position, thereby signaling the measurement and control circuits 162 via line 176 to activate the motor control 168 via line 170 for rotating the motor 120 via line 166 to unload or remove the sample material from the test cell as described above. The foregoing circuits are described in detail in the copending application of David B. Funk for "Analysis Instrument", Ser. No. 791,641, filed Apr. 27, 1977, and assigned to the assignee of this application, which is incorporated herein by reference.

While the test instrument of the present invention has been shown and described herein as a moisture tester, it will be apparent that the embodiment disclosed is equally applicable to the measuring of the contents of constituents of materials other than moisture. Thus, the instrument disclosed herein is capable of performing measurements of a plurality of constituent contents of a material as well as being adapted to measure such constituent contents of a plurality of different materials.

While a particular embodiment of the present invention has been shown and described herein, various changes may occur to those skilled in the art and will be understood as forming part of this invention insofar as they fall within the spirit and scope of the appended claims.

The invention is claimed as follows:

1. In an analysis instrument for measuring selected constituent contents of a sample of material, the combination comprising: a test cell for receiving said sample, said test cell defining a capacitor having measurable electrical properties modified in accordance with the dielectric constant of the sample, which dielectric constant is a function of the contents thereof, means for producing an output condition corresponding to the bulk density of a sample including means for adjusing the volume of the sample received in said test cell to a predetermined constant volume and weighing means for producing an output condition corresponding to the weight of said sample in said test cell, said measurable electrical properties of said capacitor and said bulk density output condition producing means coacting to give measurable outputs indicative of the selected constituent contents of said sample in the test cell.

2. The combination according to claim 1 further including temperature sensing means for producing an output corresponding to the temperature of said sample.

3. The combination according to claim 1, wherein said volume adjusting means comprises means for introducing said sample into said test cell, including hopper means mounted above said test cell for holding a supply of the material to be tested of substantially greater volume than the capacity of the test cell and selectively openable door means defining a bottom of said hopper means.

4. The combination according to claim 3 wherein said test cell has a substantially planar open top and said means for adjusting the volume of said sample received in said test cell to a predetermined constant volume further comprises strike off means mounted adjacent said test cell and selectively movable across the top thereof for striking off said material level with the top thereof.

5. The combination according to claim 4, said volume adjusting means further including means for sequentially activating said door means and said strike-off means.

6. The combination according to claim 5 wherein said means for sequentially activating said door means and said srike-off means comprises motor means, shaft means connected to said motor means for rotation thereby, cam means connected to said shaft means and rotatable in unison therewith and in engagement with said door means for selectively opening and closing said door means, and linkage means connected to said shaft means and to said strike-off means and actuated by the rotation of said shaft means for moving said strike-off means across the top of said test cell, said linkage means being positioned on said shaft means so as to actuate said strike-off means following the opening of said door means by said cam means.

7. The combination according to claim 6 further including means rotatably supporting said test cell and further motor means connected to said test cell supporting means, said further motor means being selectively activatable to rotate said test cell to empty said sample therefrom.

8. The combination according to claim 7, said means rotatably supporting said test cell comprising shaft means connected to said further motor means to be rotated thereby, a first collar attached to said test cell, a second collar attached to said shaft means and a pair of substantially planar and parallel flexure plates attached between respective top and bottom sides of said first and second collars.

9. The combination according to claim 8 wherein said weighing means comprises a coil attached to said first collar and a core member attached to said second collar and extending through the center of said coil, said flexure plates being adapted to flex in response to the weight of the sample in said test cell to provide relative movement between said first and second collars for causing a relative change of position of said core member within said coil corresponding to the weight of said sample in said test cell.

10. The combination according to claim 9 further including first stop means connected to and movable with said shaft means and second and third fixed stop means mounted for engaging said first stop means when said test cell is upright and has been rotated by said further motor means through substantially 180°, respectively, and said further motor means includes means for automatically reversing its direction of rotation when said first stop means engages either of said second and third stop means for automatically rotating said test cell back to its opposite position.

11. The combination according to claim 10, further including switch means engageable by said first stop means for providing an indication of said rotation of said test cell corresponding to said removal of said sample from said test cell.

12. In a moisture tester for measuring the moisture content of a sample of a bulk commodity, the combination comprising: a test cell for receiving said sample and having a substantially planar open top, said test cell defining a capacitor, hopper means mounted above said test cell for holding a supply of the commodity to be tested of substantially greater volume than the capacity of the test cell and selectively openable door means defining a bottom of said hopper means for introducing a sample of the commodity to be tested into the test cell, means for producing an output condition corresponding to the bulk density of a sample, which bulk density is a known function of the moisture content thereof, including strike-off means mounted adjacent said test cell and selectively movable across the top thereof for striking off said commodity level with the top of said test cell and cooperative with said hopper means and said door means to adjust the volume of said sample received in said test cell to a predetermined constant volume, said test cell capacitor having measurable electrical properties corresponding to the dielectric constant of said sample in said test cell, which dielectric constant is a known function of the moisture content thereof.

13. In a moisture tester for measuring the moisture content of a sample of a bulk commodity, the combination comprising: a test cell for receiving said sample and having a planar open top, means for adjusting the volume of said sample received in said test cell to a predetermined constant volume including strike-off means adjacent the top of said test cell for striking off excess bulk commodity to the level of said top, weighing means for producing an output condition corresponding to the weight of said predetermined volume of the sample in the test cell, and removal means for selectively removing said sample from said test cell.

14. The combination according to claim 13, wherein said strike-off means further includes a strike-off arm, motor means, shaft means connected to said motor means, linkage means connected to said shaft means and to said strike off arm and actuatable by said shaft means for moving said strike off arm across the top of said test cell.

15. In a moisture tester for measuring the moisture content of a sample of a bulk commodity, the combination comprising: a test cell for receiving said sample, means for producing a measurable output corresponding to the bulk density of said sample including means for adjusting the volume of said sample in said test cell to a predetermined constant volume and weighing means for producing a measurable output corresponding to the weight of said predetermined volume of said sample in said test cell, and removal means for selectively removing said sample from said test cell.

16. In a moisture tester for measuring the moisture content of a sample of a bulk commodity, the combination comprising: a test cell to receive said sample and having an open top, means for introducing said sample into said test cell including hopper means mounted above said test cell for holding a supply of said commodity of substantially greater volume than the capacity of said test cell and selectively operable door means defining a bottom of said hopper means, means for producing a measurable output corresponding to the bulk density of said sample said test cell and said measurable output corresponding to bulk density coacting to provide a measure of the moisture content of said sample.

17. The combination according to claim 16, further including temperature sensing means for producing an output corresponding to the temperature of said sample in said test cell.

18. The combination according to claim 17, wherein said test cell comprises a housing, a pair of substantially parallel facing electrodes mounted on said housing to define capacitor plates, a middle member mounted in said housing substantially centered between and parallel to said facing electrodes, said middle member comprising a printed circuit board having an electrode portion formed on each side thereof substantially in alignment with said facing electrodes to define further capacitor plates, said temperature sensing means being mounted within but electrically isolated from said electrode portions of said middle member, and a transverse wall member of said housing abutting said facing electrodes and abutting said middle member about said electrode portion thereof for enclosing all but said open top of said test cell.

19. In a moisture tester for measuring the moisture content of a sample of a bulk commodity, the combination comprising: a housing, a test cell for receiving said sample and having a substantially planar open top, means rotatably supporting said test cell in said housing, hopper means mounted in said housing above said test cell for holding a supply of said commodity substantially greater volume than the capacity of said test cell, selectively openable door means defining a bottom of said hopper means for introducing said sample into said test cell, weighing means attached to said rotatable supporting means for producing a measurable output corresponding to the weight of said sample in said test cell, strike-off means mounted adjacent said test cell and selectively movable across the plane of the top thereof for striking off excess grain above the planar top of said test cell, means for sequentially activating said door means and said strike-off means for filling said test cell with a predetermined volume of said sample, and means including motor means connected to said rotatable supporting means for selectively rotating said test cell to empty said sample therefrom.

20. In a moisture tester for measuring the moisture content of a sample of a bulk commodity, a test cell for receiving a sample, said test cell defining a capacitor and including a housing, a pair of facing planar electrodes mounted substantially in parallel on said housing to define capacitor plates, a middle member mounted in said housing between and parallel to said facing electrodes, said middle member comprising a printed circuit board having a planar electrode portion formed thereon substantially in alignment with said facing electrodes, and a printed circuit portion formed thereon surrounding said electrode portion and enclosed by said housing, an enclosure member abutting the facing electrodes and abutting the middle plate about the electrode portion thereof to define a test chamber having an open top to receive said sample, said electrode portion of said middle member including means for mounting temperature sensing means thereon, said enclosure member and said housing defining therebetween a chamber for containing electrical circuit components mounted upon said printed circuit portion of said middle member.

* * * * *